United States Patent [19]

Kanak, Jr.

[11] 3,992,475

[45] Nov. 16, 1976

[54] THERMAL INSULATIONS IN ACID-CATALYZED ALKYLATION PROCESS

[75] Inventor: Ernest Kanak, Jr., Missouri City, Tex.

[73] Assignee: UOP Inc., Des Plaines, Ill.

[22] Filed: Dec. 3, 1975

[21] Appl. No.: 637,445

Related U.S. Application Data

[60] Continuation-in-part of Ser. No. 591,270, June 30, 1975, abandoned, which is a division of Ser. No. 483,999, June 28, 1974, abandoned.

[52] U.S. Cl. .................. 260/683.48; 260/683.59; 260/671 R
[51] Int. Cl.² .......................................... C07C 3/54
[58] Field of Search ............... 260/683.43, 683.58, 260/683.48, 683.49, 683.69, 671 R, 671 A, 671 B

[56] References Cited

UNITED STATES PATENTS 2,546,042  3/1951  Oberfell et al. ............... 260/683.43

Primary Examiner—George Crasanakis
Attorney, Agent, or Firm—James R. Hoatson, Jr.; Robert W. Erickson; William H. Page, II

[57] ABSTRACT

A method for designing an improved process for the acid-catalyzed alkylation of hydrocarbons wherein the cost of the physical plant of the process is reduced. Thermal insulation provided for the exteriors of reaction and acid storage zones in the process reduces the required size of costly acid relief systems due to an effective decrease in the loading of those systems during the fire-emergency design case.

4 Claims, 1 Drawing Figure

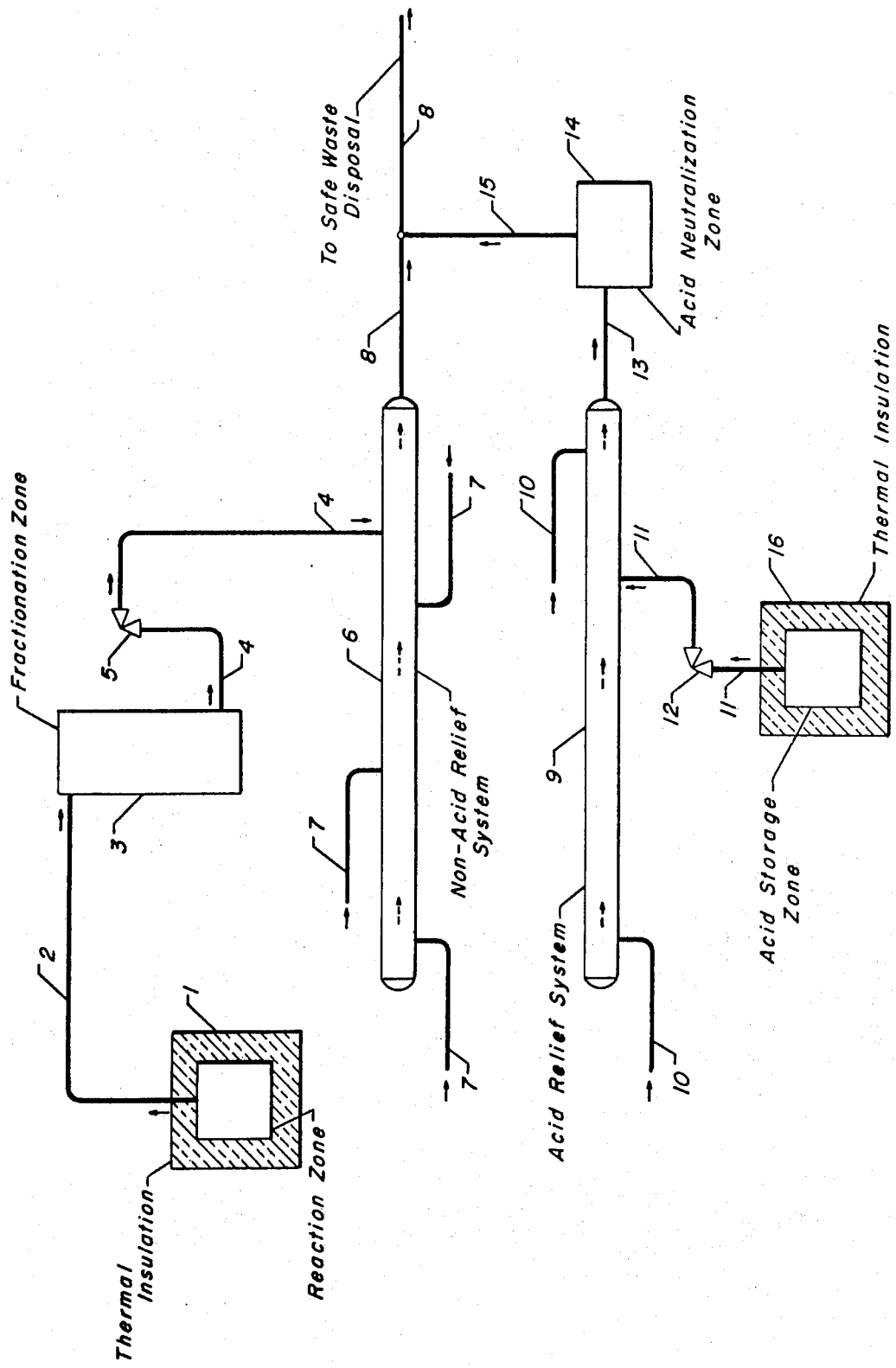

3,992,475

THERMAL INSULATIONS IN ACID-CATALYZED ALKYLATION PROCESS

CROSS-REFERENCE TO RELATED APPLICATIONS

This application is a continuation-in-part of my application Ser. No. 591,270, filed June 30, 1975 now abandoned, which is a division of application Ser. No. 483,999, filed June 28, 1974 now abandoned.

BACKGROUND OF THE INVENTION

1. Field of the Invention

The field of art to which this invention pertains is hydrocarbon processing. It particularly relates to lower capital cost in a process for the acid-catalyzed alkylation of isoparaffins with olefins.

2. Prior Art

The acid-catalyzed alkylation of hydrocarbonaceous materials is one of modern petroleum refining's most valued tools. The production of higher molecular weight isoparaffins, having valuable antiknock properties and used as motor fuel, is of considerable importance. A convenient source of such higher molecular weight isoparaffins is the acid-catalyzed alkylation of lower boiling isoparaffins, such as isobutane, with olefins such as propene and butenes. It is well known in the art that catalytic alkylation, using hydrofluoric or sulfuric acid as the catalyst, has become an important tool for preparing alkylated hydrocarbons.

Hydrofluoric and sulfuric acids are hazardous chemicals with properties peculiar to themselves which call for special handling and treatment. With improper treatment they can be lethal. For this reason processes for the use of such acids must be equipped with systems which effectively prevent the escape of these acids into the atmosphere. Common practice in the art is to provide an acid relief system which collects the effluent of all relief valves within the process from which acid may be expected to be released. As is well known in the art, relief valves are commonly fitted to processing zones which may operate at superatmospheric pressures. These valves open and allow an exhaust of material from the process at pressure levels above normal but below that at which structural damage to the processing zones would occur. It is quite common during the cessation or initiation of operation of a process that processing zones are periodically over pressured. During these periods of overpressure, the associated relief valves open and maintain safe pressure levels by exhausting material from the affected zones. The exhausts from acid-bearing relief valves pass to an acid relief system which carries the exhaust to a neutralizing zone, wherein the acid contained within the exhaust is neutralized and made safe for entry into the normal waste disposal facilities of the process. The metallurgy of acid relief systems must be such as to resist the effects of corrosion from the acid passing through it. Relatively exotic and very expensive metallurgical formulations are often used as materials in the construction of acid relief systems.

Zones within the process which do not commonly contain acid are likewise protected by relief valves, but these valves commonly exhaust into a so-called non-acid relief system. The non-acid relief and the acid relief systems of a hydrogen fluoride alkylation process are major pieces of equipment, and they represent significant portions of the capital investment involved in the realization of such a process. I have found that by a novel inclusion of thermal insulation in the design of the processing plant the size, and hence the cost, of the acid relief and non-acid relief systems can be reduced. The present invention provides for this reduction in cost, and it is fully as useful in the modification of existing processes for higher capacity as it is in the design of new installations.

OBJECTS AND EMBODIMENTS

It is an object of the present invention to provide an improved design method for processes for conducting the alkylation of isoparaffins with olefins through acid catalysis. It is a further object of my invention to provide an acid-catalyzed alkylation process of lower capital cost. A still further object of my invention is to provide a method for reducing the capital cost of design modifications made for increasing the process capacity of an acid catalyzed alkylation process.

In one embodiment my invention affords a method for designing a process for the acid-catalyzed alkylation of hydrocarbonaceous materials, which process contains relief valves and relief systems for collecting the exhausts from said relief valves, whereby the sizes of the relief systems are reduced, which method comprises the steps of: (a) providing an acid storage zone, which acid storage zone communicates with one of said relief systems through one of said relief valves; (b) providing a reaction zone for carrying on acid-catalyzed alkylation reactions, which reaction zone communicates with one of said relief systems through one of said relief valves; (c) providing thermal insulation upon the exterior of said acid storage zone to a thickness of at least 2 inches to reduce the load of exhausted material upon the relief system of step (a) during fire emergencies; and, (d) providing thermal insulation upon the exterior of said reaction zone to a thickness of at least 1 inch to reduce the load of exhausted material upon the relief system of step (b) during fire emergencies.

BRIEF SUMMARY OF THE INVENTION

My invention involves an improved design method for a process for the acid-catalyzed production of alkylated hydrocarbons which reduces the capital cost of the physical plant of the process. The design method provides thermal insulation for the reaction zone and the acid storage zone of the process will predetermined thickness of insulating material. Thermal insulation reduces the amount of heat which would be absorbed by these zones during a fire emergency in the processing plant. Reduction of the heat thus absorbed reduces the amount of acidic and hydrocarbonaceous materials which would be exhausted from process relief valves into the associated acid and non-acid relief systems. The required sizes of these costly systems are often based upon the relief valve exhaust flows during fire emergencies, and hence the required sizes, and costs, of the systems are reduced.

BRIEF DESCRIPTION OF THE DRAWING

The attached drawing illustrates a particular embodiment of the present invention. Only such details are included as are necessary for a clear understanding of my invention, and no intention is thereby made to unduly limit its scope. Certain items necessary to the operation of the process of this invention but unnecessary to its understanding, such as certain process streams, valves, pumps, instrumentation and other equipment have been omitted for the sake of clarity.

Referring now to the drawing, a hydrogen fluoride catalyzed alkylation process is schematically represented wherein thermally insulated reaction zone 1 communicates with non-acid relief system 6 through conduit 2, fractionation zone 3, conduit 4 and relief valve 5. In a condition of overpressure within the reaction and fractionation zones relief valve 5 opens and exhausts material through conduit 4 into non-acid relief system 6. This material passes through the non-acid relief system and exits in conduit 8, passing to safe waste disposal facilities. Other zones within the process, whose relief valves exhaust acid-free materials, communicate with non-acid relief system 6 through conduits 7.

Thermally insulated acid storage zone 16 communicates with acid relief system 9 through conduit 11 and relief valve 12. Relief valves in other zones of the process which exhaust acid-bearing materials communicate with acid relief system 9 through conduits 10. Acid-bearing materials exit acid relief system 9 in conduit 13 and enter acid neutralization zone 14. After neutralization of the acid, the materials exit acid neutralization zone 14 in conduit 15 and pass to conduit 8 where they intermix with non-acid materials from non-acid relief system 6. The resulting mixture of acid-free materials from non-acid relief system 6 and acid neutralization zone 14 pass in conduit 8 to safe waste disposal facilities.

DETAILED DESCRIPTION OF THE INVENTION

Acids commonly used as catalytic agents for the production of alkylated hydrocarbons, as for example hydrofluoric and sulfuric acids, are extremely hazardous substances. Hydrofluoric acid is particularly dangerous because of its effect upon all living body tissues. It is harmful in practically any concentration in either liquid or vapor form. In solution, hydrofluoric acid breaks down into hydrogen and fluorine which are present as what are known as hydrogen ions and fluorine ions. As with sulfuric acid, hydrofluoric acid causes a surface burn to bodily tissues through the action of the hydrogen ions. In addition, the fluorine ions penetrate below the surface and continue to attack and destroy the tissue and bone until they are precipitated as magnesium or calcium fluoride by the action of magnesium or calcium compounds present in the body or administered in medical treatments. The fluorine ions effect deep seated, ulcerous sores which commonly resist therapeutic efforts. The effect of the acid upon skin and mucus tissue is to cause extreme pain which often occurs only after the acid has been absorbed below the surface, such that washing is largely ineffective. This effect is commonly known to personnel of hydrogen fluoride processes as delayed-action burn.

Because of the character of these acids it is essential that they not be released into the atmosphere. For this reason elaborate and costly systems are designed into acid-catalyzed alkylation process plants to collect the exhaust of acid from the process and neutralize it before conduction to waste disposal facilities. The corrosiveness of hydrofluoric acid makes the use of expensive materials necessary. At water contents in excess of 5% in the acid the corrosion rate on mild carbon steel becomes prohibitive. Exotic materials such as Monel, copper, silver and platinum are resistant to hydrofluoric acid, except that copper and silver are attached in the presence of sulfur compounds and oxygen. It should be noted that stainless steels are, in general, less resistant to hydrofluoric acid than is mild carbon steel. Moving parts, such as those within the mechanisms of valves in the relief system, are most strenuously attacked by the acid, and specification of all Monel valving is common. The cost of these special materials makes important the minimization of size of the relief system. It is common design practice to provide conduits which connect with each acid relief valve of a process and with an acid relief system. Acid exhausting from a relief valve of the process is contained within and conducted by this system to an acid neutralization zone where neutralization of the acid takes place before passage to waste disposal. Modern alkylation process designs also provide a non-acid relief system for collection of process fluids which do not contain acid.

A relief valve is a device which permits the escape, or exhaust, of material from a processing zone which has become overpressured, a condition of pressure above the normal operating level and below the level of danger. Relief valves actuate automatically and are commonly relied upon by operators of processes to protect equipment and life during the starting and stopping of processing operations. Emergency situations which almost invariably cause the actuation of relief valves include: failure of utilities supplies, as for instance cooling water or air, electricity, steam, pressured air; mechanical equipment failure, such as failure of motors, pumps, compressors; explosion; fire; rupture of conduits; serious leaks. This invention relates to all of the above, insofar as it pertains to the design of relief systems, however it most concerns the situation of fire, commonly known to a designer as the fire-emergency design case, or more simply, the fire case. In designing a relief system the designer must consider each possible case of actuation of each relief valve and then size the relief system to accommodate the highest load of exhausted material which results from a summation of his considerations. The fire case, the existence of live flames within the process plant area, is very often the controlling case. This is because flames playing upon vessels and equipment which are not thermally insulated or are only lightly thermally insulated quickly cause vaporization of liquid within the equipment and expansion of resultant vapors. The vaporization and expansion result in increased pressure within the equipment and actuation of associated relief valves. I have found that novel provisions of thermal insulation in the design of the alkylation process can reduce the required size and cost of relief systems to an extent many times the value of the insulation required. My invention is applicable to all zones within the alkylation process which have relief valves, however, it finds its greatest utility when applied to the reaction and acid storage zones.

The decision of whether to provide thermal insulation in the design of a given zone within an alkylation process is commonly made primarily upon the basis of the undesirability of loss of heat by the zone. In other words, if a zone operates at a temperature near ambient it is general design practice in the art not to provide insulation for it, since little heat loss will occur to the atmosphere. In another case, if a zone operates higher in temperature than that of its environment and it is desired that heat be lost it will not be insulated. I have found that in order to minimize capital cost of a process the desirability of insulation of a zone must also be considered from the point of view of its effect on the size of the associated relief system. The size of a relief system required for a particular zone or process depends upon the amount of material which will be exhausted from the process relief valves in the controlling case. This treatise will be limited to a discussion of a situation in which the fire case is controlling. When a fire emergency occurs, vaporization of liquid material from all wetted surfaces within the zone begins to take place due to the intense heat transmitted to the zone by the live flames. Vaporization of liquid contributes large quantities of vapor which must pass through the relief system without significant restriction. This requirement of minimal restriction sets the size of a relief system. It is seen, therefore, that the amount of vaporized material which must pass through the relief system determines the relief system size.

Thermal insulation placed on the exterior surfaces of processing zones reduces the amount of vapor generated in the fire case. Heat conducted through the wall of a processing zone may be expressed by the following equation:

$$Q = F\ 21000 A^{0.82},$$

wherein Q is heat transferred into the zone in BTU per hour, A is the wetted, internal surface area of the zone in square feet, and F is a factor relating to the characteristics of the exterior surface. When the exterior surface of the processing zone is bare metal, F is equal to 1.0, whereas a one inch thickness of thermal insulation gives F a value of 0.3 and a three inch thickness gives F a value of 0.1. Thus, the amount of vapor generated in a fire case can be reduced by 90 percent through the application of three inches of thermal insulation to a previously uninsulated processing zone. This decrease in relieved material has a significant effect upon the size of the relief system.

The design method of my invention is particularly applicable to the reaction and acid storage zones of hydrofluoric acid-catalyzed hydrocarbon alkylation processes. Reaction zones common in the art are liquid filled vessels used for the contact of immiscible acid and hydrocarbon phases. The alkylation reaction is inherently exothermic, and it is desirable for product quality reasons that it proceed at a temperature within the range of from about 80 to about 140° F. These vessels are therefore commonly provided with internally placed heat removal means to maintain the desired zone temperature. In prior art design methods the vessels and piping are not thermally insulated so that the small amount of heat lost to the atmosphere might be beneficial in controlling the reaction zone temperature. In a fire emergency the reaction zone is invariably a major contributor of exhausted material due to its lack of thermal insulation and its large internal wetted surface. Acid storage zones are commonly constituted of vessels partially filled with liquid hydrofluoric acid held in readiness for use in the process. These vessels are sometimes provided with a thin layer of insulation, normally one inch thick. Acid storage zones are major contributors of exhausted material during fire emergencies due to the high wetted surface and to the high volatility of hydrofluoric acid.

The attached schematic drawing illustrates a process designed by the method of my invention. Reaction zone 1 and acid storage zone 16 are thermally insulated. In a fire emergency in a plant of my design only a small amount of vaporization takes place within the insulated reaction and fractionation zones. This small amount of vaporization requires a much smaller relief valve 5, piping 4 and non-acid relief system 7 than would be required if the reaction zone were not insulated. The required thickness of insulation for the reaction zone is somewhat dependent upon the thermal conductivity of the particular insulating material being used, however the reaction zone must be insulated to a thickness of at least 1 inch. A preferred range of thickness is from 2 to 4 inches.

In prior art alkylation process design methods the acid storage zone is generally provided with light thermal insulation, commonly one inch thick. My design method mandates that insulation of at least 2 inches thick be provided for the acid storage zone. This is due to the exceptional volatility of high-strength acid which is contained therein. A preferred range of thickness for the acid storage zone insulation is from 2 to 5 inches. Increased insulation in the acid storage zone reduces the amount of relieved material according to the aforesaid equation, and smaller line 11, relief valve 12 and acid relief system 9 are required than would be necessary without the increased acid storage zone insulation.

A corollary advantage of the use of the design method of my invention is found in the greater assurance that acid materials which are exhausted from reaction zone 1 will not find their way into non-acid relief system 6. Common designs depend upon the volume and heat sink properties of fractionation zone 3 to prevent passage of acid from the reaction zone to the non-acid relief system. When the reaction zone is uninsulated, a severe fire emergency can result in passage of acid from reaction zone 1 through fractionation zone 3 and relief valve 5 and into nonacid relief system 6 where severe corrosion can take place. Non-acid relief systems are not generally designed to withstand acid attack. Insulation of reaction zone 1 greatly reduces this possibility by reducing the amount of acid leaving the reaction zone in such a fire emergency.

My invention is useful for new alkylation process installations, however, it is also of utility where a design is required in the modification of existing plants for higher processing capacity. Provision of insulation according to this invention can often justify using the original relief systems with larger processing zones. Capital cost of a plant revamp, or modification, for higher capacity is thereby reduced.

Resonable variation and modification are possible within the scope of the foregoing disclosure, drawing and the claims to the invention without departing from the spirit thereof.

I claim as my invention:

1. In a process for the acid-catalyzed alkylation of hydrocarbon feeds, which process includes relief valves and relief systems for collecting the exhausts from said relief valves, the improvement which consists of reducing the size of said relief systems, said process comprises the steps of:
    a. providing an acid storage zone for the acid catalyst used in said alkylation, said acid storage zone communicating with one of said relief systems through one of said relief valves;
    b. providing a reaction zone for said acid-catalyzed alkylation of said hydrocarbon feeds said reaction zone communicating with another of said relief systems through one of said relief valves;

c. providing thermal insulation upon the exterior of said acid storage zone to a thickness of at least 2 inches to reduce the load of exhausted material upon the relief system of step (a) during fire emergencies; and, d. providing thermal insulation upon the exterior of said reaction zone to a thickness of at least 1 inch to reduce the load of exhausted material upon the relief system of step (b) during fire emergencies.

2. The method of claim 1 further characterized in that said acid is sulfuric acid.

3. The method of claim 1 further characterized in that said acid is hydrofluoric acid.

4. The method of claim 1 further characterized in that said alkylation process produces alkylated hydrocarbons from said feeds comprising isoparaffins and olefins.

* * * * *